United States Patent [19]

Michelet

[11] 4,297,284
[45] Oct. 27, 1981

[54] PREPARATION OF 2,3-DIHYDRO-2,2-DIMETHYL-7-HYDROXYBENZOFURAN

[75] Inventor: Daniel Michelet, Tassin la Demi-Lune, France

[73] Assignee: Rhone-Poulenc Agrochimie, Lyons, France

[21] Appl. No.: 171,087

[22] Filed: Jul. 22, 1980

Related U.S. Application Data

[63] Continuation of Ser. No. 170,977, Jul. 18, 1980, abandoned.

[30] Foreign Application Priority Data

Jul. 18, 1979 [FR] France ............................... 79 19127

[51] Int. Cl.$^3$ .......................................... C07D 307/86
[52] U.S. Cl. ................................ 260/346.22; 568/766
[58] Field of Search .................... 260/346.22; 568/766

[56] References Cited

U.S. PATENT DOCUMENTS 3,320,286  5/1967  Franko-Filipasic ............ 260/346.22
3,474,170 10/1969  Scharpf ............................... 424/285

FOREIGN PATENT DOCUMENTS 1139001  1/1969  United Kingdom .

OTHER PUBLICATIONS

Martini et al., J. Org. Chem., vol. 35, No. 9, 1970, pp. 2904–2907.

*Primary Examiner*—Henry R. Jiles
*Assistant Examiner*—Bernard Dentz
*Attorney, Agent, or Firm*—Burns, Doane, Swecker & Mathis

[57] ABSTRACT

2,3-Dihydro-2,2-dimethyl-7-hydroxybenzofuran is prepared by heating isobutenylpyrocatechol or isobutenylpyrocatechol/methallylpyrocatechol admixtures, at cyclization/isomerization temperatures, in the presence of a catalytic amount of an organic sulfonic acid.

14 Claims, No Drawings

PREPARATION OF 2,3-DIHYDRO-2,2-DIMETHYL-7-HYDROXYBENZOFURAN

CROSS-REFERENCE TO RELATED APPLICATION

This application is a continuation of my copending application, Ser. No. 170,977, filed July 18, 1980 (and now abandoned), assigned to the assignee hereof and hereby expressly incorporated by reference in its entirety and relied upon.

BACKGROUND OF THE INVENTION

2. Field of the Invention

The present invention relates to an improved process for the preparation of 2,3-dihydro-2,2-dimethyl-7-hydroxybenzofuran from isobutenylpyrocatechol and/or methallylpyrocatechol.

2,3-Dihydro-2,2-dimethyl-7-hydroxybenzofuran (hereinafter, often simply "DDHB") is a compound having the structural formula:

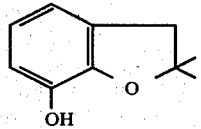

Such compound is also designated 7-hydroxy-2,2-dimethylcoumaran.

DDBH is a known compound which is useful, in particular, as an intermediate in the synthesis of the insecticide carbofuran (2,3-dihydro-2,2-dimethylbenzofuranyl methylcarbamate).

Isobutenylpyrocatechol, as intended herein, is the compound 3-isobutenyl-1,2-dihydroxybenzene having the structural formula:

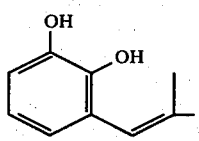

And methallylpyrocatechol, also as intended herein, is the compound 3-methallyl-1,2-dihydroxybenzene having the structural formula:

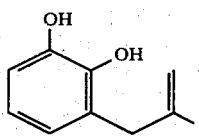

Methallylpyrocatechol is a compound which can be prepared by thermal isomerization of ortho-methallyloxyphenol; such isomerization is typically carried out by heating the parent compound at a temperature between 150° and 250° C., preferably in a medium diluted with a solvent.

Isobutenylpyrocatechol is a compound which can be prepared by prolonged heating, in bulk, of methallylpyrocatechol, preferably in contact with a metal surface, and with the subsequent elimination of any unreacted methallylpyrocatechol; such elimination can be carried out, e.g., chemically, the methallylpyrocatechol being converted into DDHB by heating (at a temperature between 100° and 250° C.) in the presence of water.

This invention especially relates to an economic process for the preparation of DDHB from isobutenylpyrocatechol, or admixtures thereof with methallylpyrocatechol.

2. Description of the Prior Art

The conversion of alkenylphenols into heterocyclic aryl compounds can be deemed either a cyclizing isomerization or an isomerizing cyclization.

The cyclizing isomerization of alkenylphenols has long been known to the art: in 1913, for example, German Pat. No. 279,864 described the conversion of allylphenol or allylcresol into methallylcoumaran in the presence of HBr or pyridine hydrochloride.

However, the preparation of compounds of the benzofuran type from compounds of alkenylphenol type is a much more complicated reaction than the simple cyclizing isomerization of an allylphenol, in particular, because of the risk that the isomerization might proceed in the direction of compounds other than the desired products.

In general, Claisen et al. [*Ann.*, 442, page 228 (1925)] have concluded that the isomerization of simple allylphenol does indeed lead to compounds to benzofuran or coumaran type, in accordance with the equation:

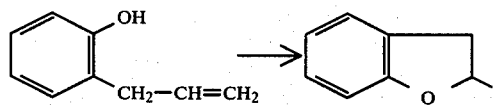

but that, on the other hand, the presence of substituents on the terminal carbon of the double bond leads to compounds of chroman type, in accordance with the equation:

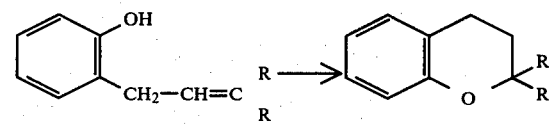

such being the case even if one of the radicals R represents hydrogen.

The immediately aforesaid is confirmed by more recent work, such as that of Frater et al. [*Helv. Chim. Acta*, 50, pages 255–256 (1967)] and Piccardi et al. [*J. Chem. Soc.*, Perkin I, page 624 (1977)].

Certain methallylmonophenols too have been isomerized into benzofuran compounds by catalysis in an acid medium (isopropylmethallylphenol in U.S. Pat. Nos. 3,876,667 and 3,816,473 and acetylmethallylphenol in U.S. Pat. No. 3,419,579), but it is considered that, below 150° C., the reaction proceeds too slow to be an acceptable process, with the result that the preferred temperatures are above 175° C. (U.S. Pat. No. 3,419,579) or even above 200° C. (U.S. Pat. Nos. 3,876,667 and 3,816,473).

In the particular case of monophenols substituted by nitro or bromo groups, it is reported (British Pat. No. 1,139,001 and French Pat. No. 1,472,283) that the corresponding methallylphenols and isobutenylphenols can be cyclized/isomerized in the presence of catalysts, at above 100° C. However, temperatures above 150° C. are still preferred and the foregoing patents do not allude to the cyclizing isomerization of isobutenylphenols, but only of nitro- or bromo-methallylphenol, in the presence of a catalyst of HBr/acetic acid type.

The isomerization of methallylphenol is obviously a simpler reaction than the isomerization of isobutenylphenol because, as Claisen et al. had already reported, the substituents on the terminal carbon of the double bond tend to direct the cyclizing isomerization in the direction of compounds other than benzofuran compounds.

Furthermore, the isomerization of isobutenylphenols is also a much more difficult reaction because of the fact that the double bond in the isobutenyl substituent is in a conjugated position relative to the aromatic nucleus; this chemical configuration, resembling that existing in the case of styrene, favors polymerization reactions at the expense of isomerization.

However, the cyclizing isomerization of isobutenylphenol has been expressly described by Martini et al. [*J. Org. Chem.*, 35(9), 2,904–2,906 (1970)], who report that, in order to obtain a suitable yield (84%), it is necessary to heat the isobutenylphenol in question (5-methyl-2-isobutenylphenol) in the presence of $MgCl_2$ for 8.5 hours at 184°–194° C.

Thus, all of the prior art would appear to be in agreement that:

(i) The isomerization of alkenylphenols substituted on the terminal carbon of the double bond is a difficult reaction;

(ii) Certain very special substituents can facilitate this isomerization, but only nitro and bromo groups are known to exert such influence;

(iii) Only relatively harsh and special conditions of temperature and reaction time can normally permit the conversion of an isobutenylphenol into a benzofuran; and (iv) The cyclizing isomerization of isobutenylphenols is a much more difficult reaction than the isomerization of allylphenols.

Nonetheless, all of the aforesaid prior art in fact relates only to alkenylmonophenols. The isomerization of alkenylpyrocatechol has scarcely been mentioned. In French Pat. No. 1,430,952, only the cyclization of allylpyrocatechol is reported, but no mention is made as regards the cyclization of isobutenylpyrocatechol. Furthermore, U.S. Pat. Nos. 3,816,473 and 3,876,667 advise against the use of pyrocatechol (designated simply as "catechol") in the synthesis of carbofuran intermediates, because of the presence of the two reactive hydroxyl groups and because of the tendency of pyrocatechol to give rise, on the one hand, to large amounts of undesirable by-products, and, on the other hand, to desired products of but mediocre purity.

SUMMARY OF THE INVENTION

Accordingly, a major object of the present invention is the provision of an improved catalytic process for the preparation of DDHB from isobutenylpyrocatechol and admixtures thereof with methallylpyrocatechol, which process not only enables attainment of all of those desiderata above outlined, but also is conspicuously devoid of those disadvantages and drawbacks, also above outlined.

Briefly, this invention features a process for the preparation of 2,3-dihydro-2,2-dimethyl-7-hydroxybenzofuran (DDHB), comprising heating isobutenylpyrocatechol (3-isobutenyl-1,2-dihydroxybenzene), optionally admixed with methallylpyrocatechol (3-methallyl-1,2-dihydroxybenzene), in the presence of a catalyst including an organic sulfonic acid.

DETAILED DESCRIPTION OF THE INVENTION

More particularly according to this invention, the starting material alkenylpyrocatechols typically comprise between 10 and 100% by weight of isobutenylpyrocatechol, and more advantageously at least 30% by weight of isobutenylpyrocatechol.

The reaction temperature is advantageously between 60° and 200° C., preferably between 80° and 150° C. High temperatures, and even temperatures higher than 200° C., can of course be used, but this does not constitute a significant economic advantage.

The catalysts which preferably are employed are compounds of the formula $R—SO_3H$, R being an organic radical. More particularly, R can be an alkyl, alkenyl, aryl, arylalkyl or arylalkenyl radical, the alkyl or alkenyl chains generally having fewer than 17 carbon atoms and preferably fewer than 7 carbon atoms; the preferred aryl groups are phenyl and naphthyl groups; these various radicals, in particular the aromatic radicals, can also be substituted, in particular with alkyl, hydroxyl, alkoxy and aryloxy substituents.

The following representative sulfonic acids are exemplary: benzenesulfonic acid, o-, m- and p-toluenesulfonic acids, o-, m- and p-ethylbenzenesulfonic acids, o-, m- and p-cumenesulfonic acids, o-, m- and p-tert.-amylbenzenesulfonic acids, o-, m- and p-hexylbenzenesulfonic acids, o-xylene-4-sulfonic acid, para-xylene-2-sulfonic acid, meta-xylene-4- or -5-sulfonic acid, mesitylenesulfonic acid, durenesulfonic acid, pentamethylbenzenesulfonic acid, ortho-dipropylbenzene-4-sulfonic acid, para-diisopropylbenzenesulfonic acid, alpha- and beta-naphthalenesulfonic acids, o-, m- and p-biphenylsulfonic acids, alpha-methyl-beta-naphthalenesulfonic acid, para-hydroxybenzenesulfonic acid, para-phenoxybenzenesulfonic acid, methanesulfonic acid, ethanesulfonic acid, propane-1-sulfonic acid, butane-1-sulfonic acid, methallylsulfonic acid, isobutylsulfonic acid, hexane-1-sulfonic acid, decane-1-sulfonic acid and dodecane-1-sulfonic acid.

The concentration of catalyst in the reaction medium is desirably between 0.001 and 5% by weight, preferably between 0.1 and 1%.

The process according to the invention is preferably carried out in a homogeneous phase; the nature and the concentration of the sulfonic acid are therefore most frequently selected such that the reaction medium is homogeneous under the reaction conditions.

According to another and preferred method for carrying out the process of the invention, the reaction is conducted in the presence of an inert liquid solvent (i.e., a solvent which is chemically inert under the operating conditions). The nature of the solvent is not critical; however, non-basic solvents are preferred. Aromatic, aliphatic and cycloaliphatic hydrocarbons, aromatic ethers, aliphatic, aromatic or cycloaliphatic chlorohydrocarbons and nitriles are thus particularly suitable.

The following are exemplary of solvents which can be used: benzene, toluene, ethylbenzene, xylenes (o-, m- and p-), cyclohexane, hexane, octane, dodecane, chlorobenzene, 1,2-dichloroethane, 1,1,2-trichloroethane, anisole and methylcyclohexane.

The concentration of the methallyl- and isobutenylpyrocatechols in the reaction medium is advantageously between 1 and 50% by weight, preferably between 3 and 20%.

The process according to the invention is most notable by virtue of the fact that it offers the possibility of conducting the reaction at moderate temperatures, employing moderate reaction times.

In order to further illustrate the present invention and the advantages thereof, the following specific examples are given, it being understood that same are intended only as illustrative and in no wise limitative.

EXAMPLE 1

Cyclizing Isomerization

A mixture (0.1138 g) of isobutenylpyrocatechol and methallylpyrocatechol, in the respective proportions of 38.6 and 61.4 by weight, was added to a solution (2 cc), at 100° C., of benzenesulfonic acid in toluene, having a concentration of 43.5 millimols/liter.

The mixture was heated for 30 minutes under reflux and then cooled; an aqueous solution of sodium bicarbonate (5 cc) was added, the mixture was separated by decantation and the product phase was filtered. This gave DDHB (0.108 g; yield 94.9%).

EXAMPLE 2

Preparation of Isobutenylpyrocatechol

Ortho-methallyloxyphenol (50 g) and octane (450 cc) were introduced into a 1.5 liter stainless steel autoclave provided with an argon atmosphere.

The mixture was heated for 1 hour 57 minutes at 200° C. Same was cooled, the octane was evaporated off and the residue was distilled under an absolute pressure reduced to 0.14 mm Hg (at the top of the column); the distillation apparatus was a glass apparatus which was fitted with a distillation column filled with a "knit" packing consisting of a knitted stainless steel gauze (height: 40 cm; diameter: 3 cm).

The distillation time was 5 hours 20 minutes. The last distillation fractions provided a mixture (10.06 g) containing 45% of o-isobutenylpyrocatechol and 55% of orthomethallylpyrocatechol. This mixture was a white solid melting at 55°–57° C. Recrystallization from hexane gave a mixture in the proportions of 38.6 and 61.4, which melts at the same temperature.

The latter mixture (1.0522 g), octane (10 cc) and water (5 cc) were introduced into a 50 cc titanium autoclave.

After cooling, the mixture was separated by decantation and the aqueous phase was extracted with ethyl acetate. The organic phases were combined and evaporated and the residue was recrystallized from hexane. A white wettable powder (0.2 g) consisting of 3-isobutenyl-1,2-dihydroxybenzene (purity 91%) was isolated.

This isobutenylpyrocatechol exhibited the following characteristics in nuclear magnetic resonance (NMR) carried out on the nucleus of the $^{13}C$ isotope of carbon ($^{13}C$ NMR spectrum) in deuterated DMSO, using tetramethylsilane as the reference compound:

| Group | δ in ppm |
|---|---|
| $CH_3$ | 19.1 |
| $CH_3$ | 25.9 |
| Benzene nucleus | 113.3; 118.0; 120.2; 125.6; 142.6; 144.8 |
| Ethylenic carbon atoms | 120.8; 133.2 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of 2,3-dihydro-2,2-dimethyl-7-hydroxybenzofuran, comprising heating a member selected from the group consisting of 3-isobutenyl-1,2-dihydroxybenzene, and admixture of at least 10% by weight of 3-isobutenyl-1,2-dihydroxybenzene with 3-methallyl-1,2-dihydroxybenzene, at cyclization-/isomerization temperatures, in the presence of a catalytic amount of an organic sulfonic acid.

2. The process as defined in claim 1, wherein said heating is at a temperature of from 60° to 200° C.

3. The process as defined in claim 2, wherein said heating is at a temperature of from 80° to 150° C.

4. The process as defined by claims 1 or 2, wherein said sulfonic acid has the formula $R—SO_3H$, and wherein R is selected from the group consisting of alkyl, alkenyl, aryl, arylalkyl and arylalkenyl.

5. The process as defined by claim 4, wherein said sulfonic acid is selected from the group consisting of benzenesulfonic acid, o-, m- and p-toluenesulfonic acid, o-, m- and p-ethylbenzenesulfonic acid, o-, m- and p-cumenesulfonic acid, o-, m- and p-tert.-amylbenzenesulfonic acid, o-, m- and p-hexylbenzenesulfonic acid, o-xylene-4-sulfonic acid, paraxylene-2-sulfonic acid, meta-xylene-4- or -5-sulfonic acid, mesitylenesulfonic acid, durenesulfonic acid, pentamethylbenzenesulfonic acid, ortho-dipropylbenzene-4-sulfonic acid, para-diisopropylbenzenesulfonic acid, alpha- and beta-naphthalenesulfonic acid, o-, m- and p-biphenylsulfonic acid, alpha-methylbeta-naphthalenesulfonic acid, para-hydroxybenzenesulfonic acid, para-phenoxybenzenesulfonic acid, methanesulfonic acid, ethanesulfonic acid, propane-1-sulfonic acid, butane-2-sulfonic acid, decane-1-sulfonic acid and dodecane-1-sulfonic acid.

6. The process as defined by claim 4, wherein the reaction is carried out in the presence of an inert organic solvent.

7. The process as defined by claims 1 or 2, wherein the reaction medium is homogeneous.

8. The process as defined by claims 1 or 2, wherein the concentration of the sulfonic acid in the reaction medium ranges from 0.001 to 5% by weight.

9. The process as defined by claim 8, wherein said concentration of the sulfonic acid ranges from 0.1 to 1% by weight.

10. The process as defined by claim 8, wherein the concentration of the methallyl- and isobutenyl-1,2 dihydroxybenzenes in the reaction medium ranges from 1 to 50% by weight.

11. The process as defined in claim 10, wherein said concentration of the methallyl- and isobutenyl-1,2 dihydroxybenzenes ranges from 3 to 20% by weight.

12. The process as defined by claim 6, wherein said solvent is selected from the group consisting of aliphatic and cycloaliphatic hydrocarbons or chlorohydrocarbons, aromatic ethers and nitriles.

13. The process as defined by claim 4, wherein the reaction medium is homogeneous.

14. The process as defined by claim 4, wherein the concentration of the sulfonic acid in the reaction medium ranges from 0.001 to 5% by weight, and the concentration of the methallyl- and isobutenyl-1,2 dihydroxybenzenes in the reaction medium ranges from 1 to 50% by weight.

* * * * *